United States Patent [19]

Brinkley

[11] Patent Number: 5,339,467
[45] Date of Patent: Aug. 23, 1994

[54] HANG-TYPE EARMUFF AND METHOD OF MANUFACTURE

[75] Inventor: Herman E. Brinkley, Lawrenceville, Ill.

[73] Assignee: Nu-Life Inc. of Illinois, Lawrenceville, Ill.

[21] Appl. No.: 289,697

[22] Filed: Dec. 27, 1988

Related U.S. Application Data

[63] Continuation-in-part of Ser. No. 219,224, Jul. 15, 1988, abandoned.

[51] Int. Cl.⁵ .............................................. A61F 11/00
[52] U.S. Cl. ........................................................ 2/209
[58] Field of Search ................. 2/209, 174, 275, 243 R

[56] References Cited

U.S. PATENT DOCUMENTS

| | | | |
|---|---|---|---|
| 2,378,398 | 6/1945 | Fiedler | 2/209 |
| 2,582,907 | 1/1952 | Kaufmann | 2/209 |
| 3,112,493 | 12/1963 | Greenberg | 2/209 |
| 4,713,843 | 12/1987 | Duncan | 2/209 |
| 4,791,684 | 12/1988 | Schwartz | 2/209 |
| 4,872,219 | 10/1989 | Duncan | 2/209 |

*Primary Examiner*—Peter Nerbun
*Attorney, Agent, or Firm*—Wood, Phillips, VanSanten, Hoffman & Ertel

[57] ABSTRACT

A hang-type earmuff has a unitary, seamless core of flexible plastic in a truncated, conical configuration. A cover extends across the convex outer surface of the core and a liner extends across the concave inner surface of the core. The liner is attached to the core by providing a sheet of lining material, securing the lining material to the convex outer surface of the core adjacent the central opening thereof, removing the central portion of the lining material corresponding with the core opening, folding the lining material over the edge of the core defining the opening, through the opening and across the concave inner surface of the core and securing the lining material at the peripheral edge of the core. The cover is fitted to the core over a fixture to provide ample material to extend around the wearer's ear. The cover may be sewn or welded to the liner.

24 Claims, 2 Drawing Sheets

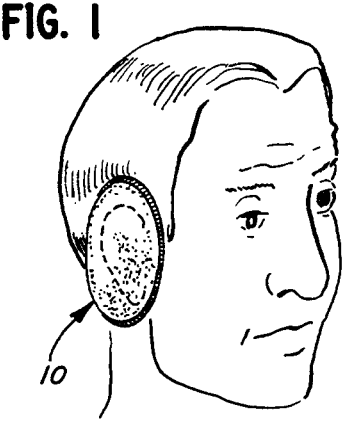
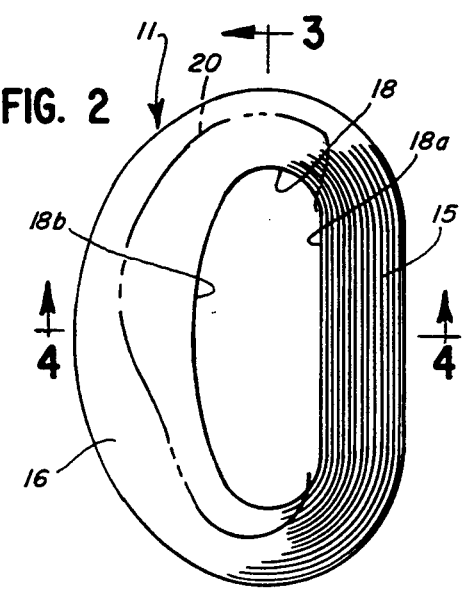
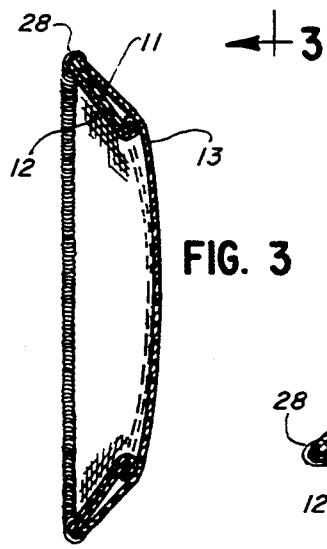
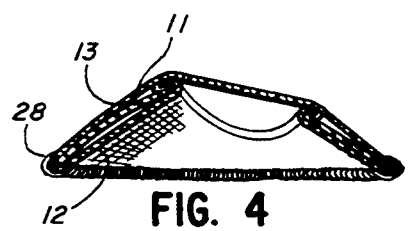
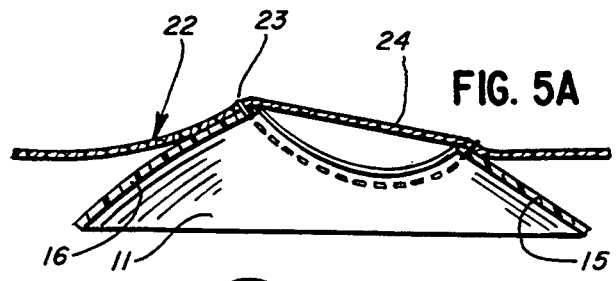
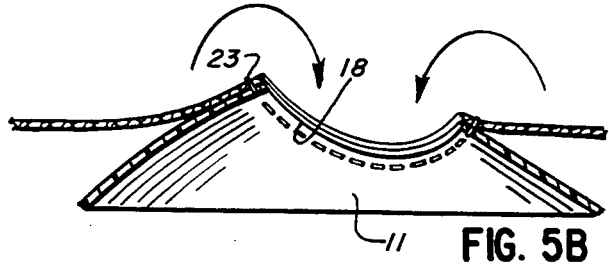
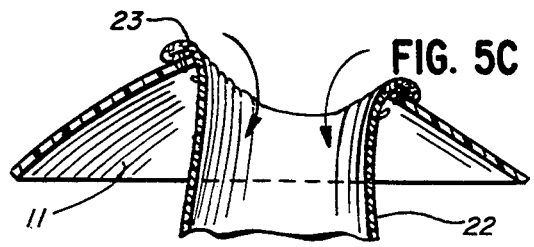
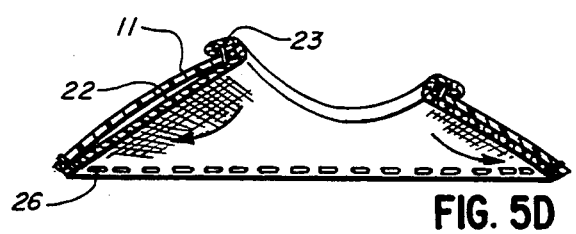
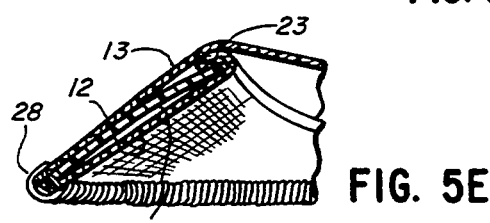
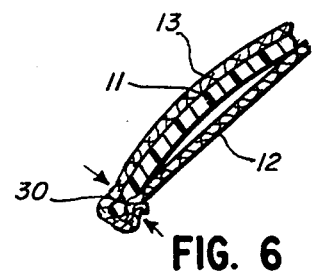

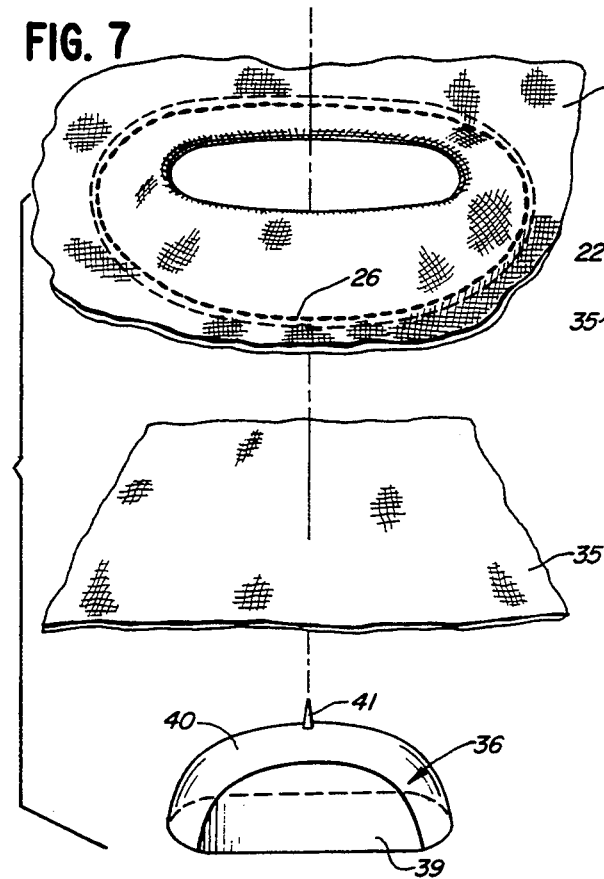
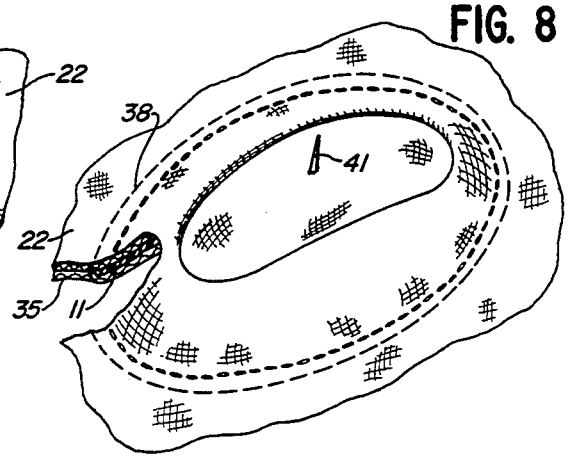
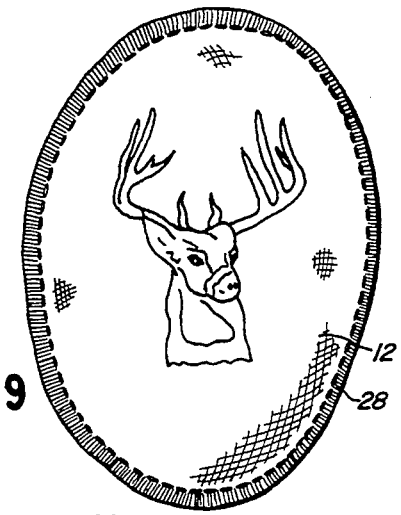
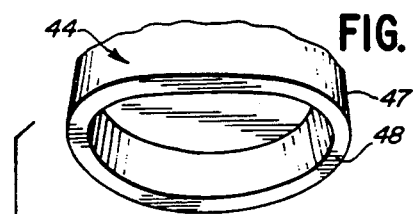
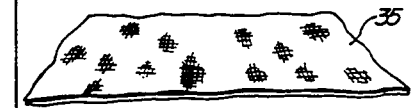
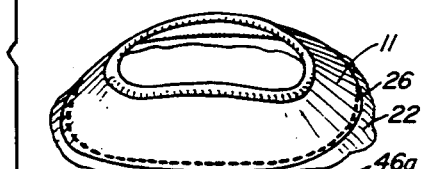
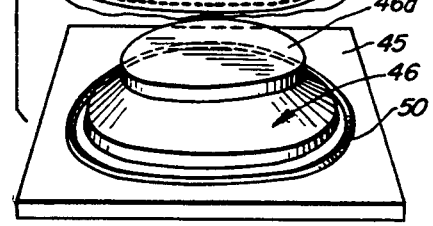
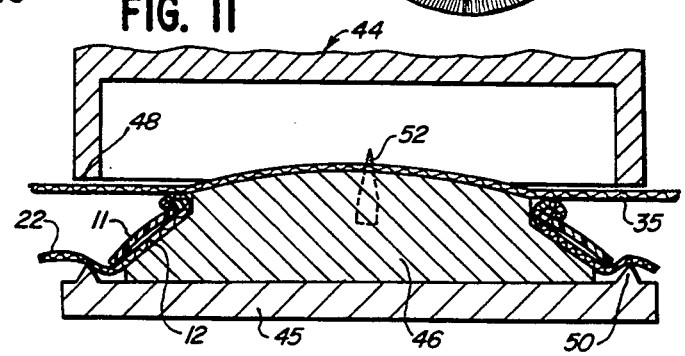
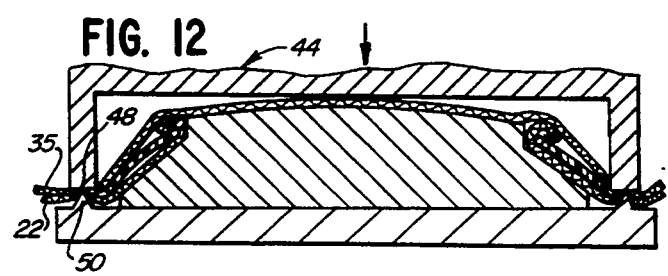

HANG-TYPE EARMUFF AND METHOD OF MANUFACTURE

This application is a continuation-in-part of Brinkley Ser. No. 219,224, filed Jul. 15, 1988, now abandoned.

FIELD OF THE INVENTION

This invention is concerned with an earmuff which hangs on the wearer's ear and with a method of manufacturing the earmuff.

BACKGROUND OF THE INVENTION

Prior hang-type earmuffs are shown in the U.S. Pat. Nos. of Fiedler 2,378,398, Kaufmann 2,582,907, Greenberg 3,112,493 and Duncan 4,713,843. The core member of the Kaufmann muff is a flat panel with a hole for the wearer's ear. Each of Fiedler, Greenberg and Duncan has a truncated conical core formed from a flat panel by cutting away a section and taping or bonding the cut edges together. These cores tend to be stiff in the area of the joint and the taped versions are bulky.

BRIEF DESCRIPTION OF THE INVENTION

A principal feature of the invention is that the earmuff has a unitary, seamless core of flexible plastic. Flexibility is uniform throughout the core and the earmuff readily conforms with the wearer's ear and head.

Another feature is that the liner for the concave surface of the core is attached to the outer convex surface adjacent the central opening. The liner extends around the edge of the opening, across the inner concave core surface and is secured at the periphery of the core.

A further feature of the invention is the method of attaching the liner to the core which includes the steps of providing the core, providing a sheet of lining material, securing the lining material to the convex outer surface of the core adjacent the central opening, removing the central portion of the lining material corresponding with the opening, folding the lining material over the edge of the core defining the opening, through the opening and across the concave inner surface of the core and securing the lining material at the peripheral edge of the core.

And another feature is the method of attaching a cover to the earmuff which includes the steps of mating a core and liner, the liner extending beyond the core, with a sheet of cover material and securing the cover material to the lining material outside the periphery of the core. More particularly, in one form of the invention, a fixture is provided to extend through the central opening of the core. A sheet of cover material is draped over the fixture. The core and liner, with the core inverter and the liner outside, is placed over the fixture and cover material. Lastly, the cover material is secured to the lining material. In another form of the invention, the core and liner are placed over a fixture with the liner inside, a sheet of cover material is draped over the core and fixture and the cover material and liner material are sonically welded outside the periphery of the core.

Yet a further feature is the attaching method in which the cover material has a design and in which the cover material is secured in position with respect to the fixture to establish the position of the design with respect to the core.

Another feature is that the earmuff core is inverted, loosening the cover, before hanging the earmuff on the wearer's ear. The core is then reinverted.

Further features and advantages will readily be apparent from the following specification and from the drawings, in which:

FIG. 1 illustrates the earmuff on a wearer's ear;

FIG. 2 is a view of the core, looking at the convex outer surface, with an outline of the wearer's ear shown in broken lines;

FIG. 3 is a section taken along the major axis of the elliptical core;

FIG. 4 is a section taken along the minor axis of the elliptical core;

FIG. 5, comprising FIGS. 5A-E, are a series of sectional views of the core, as in FIG. 4, showing the method for attaching the lining material to the core;

FIG. 6 is a fragmentary detail showing the lining and cover materials welded to the core;

FIG. 7 is an exploded perspective illustrating one method of attaching the cover to the core and liner;

FIG. 8 is a perspective of the assembled earmuff of FIG. 7;

FIG. 9 is an elevation of the outside of the completed earmuff;

FIG. 10 is an exploded perspective illustrating another method of attaching the cover to the core and liner;

FIG. 11 is a section of the assembled parts of FIG. 10, illustrating a step in the assembly of the earmuff using sonic welding; and FIG. 12 is a section similar to FIG. 11 showing welding and trimming of the liner and cover.

A hang-type earmuff 10 is slipped over the wearer's ear as seen in FIG. 1. The earmuff has a core 11, FIG. 2, with a liner 12 and cover 13, FIGS. 3 and 4. Both the liner and the cover are of a suitable sheet material, as a fabric.

The core 11 is a seamless unitary element of thin, flexible plastic, for example, a polyethylene plastic having a thickness of the order of 0.025 inch. The core is a truncated cone with an elliptical outline, irregular about the major axis, and is preferably manufactured by injection molding. The forward portion 15 of the core is substantially straight and parallel with the major axis of the core. The rear portion 16 of the core is arcuate. The core has a central opening 18 which is elliptical in outline, similar to the irregular elliptic configuration of the core. The opening has a forward edge 18a which is straight and an arcuate rear edge 18b. The core is symmetrical about its minor axis; and the earmuff can be worn on either ear.

The forward portion 15 of the core 11 is substantially planar to lie flat against the wearer's head in front of the ear, shown in broken lines at 20. The rear portion 16 of the core is curved along the minor axis about a center on the inner surface side of the core. The rear portion of the core lies beneath and behind the wearer's ear, against the side of the wearer's head.

The method of attaching the liner 12 and cover 13 is illustrated in FIG. 5. A sheet 22 of lining material, slightly larger than the core 11, is placed over the core and stitched to the core around the central opening 18, as shown at 23, FIG. 5A. The central portion 24 of the lining material corresponding with the core opening 18 is then cut away, FIG. 5B. The lining material 22 is then folded over the edge of the core defining the opening 18, through the opening, FIG. 5C, and across the concave inner surface of the core, FIG. 5D. The lining material is secured at the peripheral edge of the cover as by stitching 26. Any excess lining material is trimmed away. The cover 13 is placed over the convex outer surface of the core and secured around the periphery as by stitching, FIG 5E. The liner and cover may be secured at the periphery by the same stitching. A suitable binding, as a whip stitch 28, which may be performed by a Merrow sewing machine, finishes the raw edges of the liner and cover.

Alternatively, the edges of the cover and liner may be bonded together and to the periphery of the core as by a sonically formed weld 30, FIG. 6.

Further details of a method of securing the cover to the earmuff core and liner are illustrated in FIGS. 7 and 8. A core 11 with a sheet 27 of lining material attached by stitching at 23 and 26, as shown in FIG. 5D, is provided, with the core inverted so that the liner is on the convex outer surface. The sheet 22 of lining material is not trimmed but extends out beyond the core. A sheet 35 of cover material is draped over a fixture 36 and the core and liner are mated with the sheet of cover material and with the fixture. The center of the sheet of cover material extends into the core opening 18. The cover material 35 is then secured with the lining material 22, outside the peripheral edge of the core 11. Stitching as shown at 38, FIG. 8, may be used. The excess cover and lining materials are trimmed away and the edge may be bound.

The fixture 36 has a flat base which may be fixed to a table or other support surface (not shown). The fixture has a semi-oval shape to fit into the concave inner surface of the inverted core 11. The flat faces (one face 39 is shown, the other is on the back side as viewed in FIG. 7) are spaced a distance of the order of the width of core opening 18. The upper edge 40 of the fixture is rounded. Use of the fixture which extends into the opening 18 to support the sheet 35 of cover material ensures ample cover material to fit loosely over the wearer's ear.

Where the cover has a design, it may be desirable to position the design accurately with respect to the core. Fixture 36 has a pin 41 which extends upwardly from the top of the rounded edge 40. The sheet 35 of cover material is impaled on the pin, positioning the design with respect to fixture 36 and thus with respect to the earmuff core 11. The resulting earmuff, FIG. 9, has the deer design on the outer surface of the cover 13 centered on the earmuff. The edge is bound with a whip stitch 28 as in FIG. 5E.

An alternate manufacturing procedure is illustrated in FIGS. 10–12, using sonic energy to weld the cover and liner and to trim away excess material. A sonic welding machine (not shown) has a tool 44 which is reciprocable with respect to a base 45 and fixture 46. Tool 44 has a cylindrical body 47 connected with a sonic driver and an annular working surface 48. The tool body 47 conforms with the peripheral shape of core 11 and is slightly larger than the core. Base 45 is a steel plate with a conical aluminum fixture 46 which receives the earmuff core and liner. A cylindrical extension 46a at the top of the fixture projects through the core opening 18. A knife-edge 50 on base 45 surrounds the fixture 46.

Core 11 with a sheet 22 of lining material attached, and in its uninverted condition with the lining on the inner surface, is placed over fixture 46. Sheet 35 of cover material is draped over the fixture and core, FIG. 11. The cylindrical extension 46a of the fixture is preferably crowned slightly so that the draped cover material is loose and has sufficient room to receive the wearer's ear. Sheets 22 of lining material and 35 of the cover material extend outwardly beyond knife edge 50.

Tool 44 is lowered into contact with the cover at the knife edge. A burst of sonic energy is applied which seals the cover and liner at a point outside the peripheral edge of core 11, FIG. 12. Simultaneously with sealing of the lining and cover materials, the materials are cut separating the excess material outside the seal, completing assembly of the earmuff. If the cover has a design to be centered, a positioning pin 52 is fitted in the fixture as shown in broken lines in FIG. 11.

Attachment of the muff to the wearer's ear is facilitated by inverting the flexible core so that the concave outer surface becomes convex. This loosens the cover and the muff may readily be slipped over the wearer's ear. As stated hereinabove, flexibility is uniform throughout the unitary seamless core. Therefore, as the core is flexed to invert it, the flexing is unitary throughout said core. The core is then reinverted so that the muff lies against the side of the wearer's head.

I claim:

1. A hang-type earmuff, comprising:
    a truncated conical unitary seamless core of flexible plastic having an irregular elliptical outline and a similar elliptical central opening through which the wearer's ear extends, with a generally straight forward portion which is generally parallel with the major axis of the core and lies in front of the wearer's ear and a generally arcuate rear portion which lies beneath the wearer's ear;
    a liner of sheet material on the concave inner surface of the core; and
    a cover of sheet material on the convex outer surface of the core.

2. The earmuff of claim 1 in which the core is symmetric about the minor axis of the core.

3. The earmuff of claim 1 in which the forward portion of the core is planar along the minor axis of the core and the rear portion of the core is concave along the minor axis of the core to conform to the wearer's head behind the wearer's ear.

4. The earmuff of claim 1 in which the core has a thickness of the order of 0.025 inch.

5. The earmuff of claim 1 in which the liner and cover materials are fabric.

6. The earmuff of claim 1 in which the liner has a central opening complementary with the core opening configuration, the lining material being secured to the outer surface of the core adjacent the central opening and extending over the edge of the core defining the opening and across the inner surface of the core, the outer edge of the lining material being secured adjacent the outer edge of the core.

7. The earmuff of claim 1 with stitching securing the liner and cover to the core.

8. The earmuff of claim 1 with a weld securing the peripheral edges of the liner and cover to the core.

9. A method of attaching a liner of sheet material lining to a truncated conical unitary seamless core of flexible plastic of a hang-type earmuff the method comprising:
    securing the lining material to a convex outer surface of the core adjacent a central opening thereof;
    removing a central portion of the lining material corresponding with said opening;

folding the lining material over an edge of the core defining the opening, through the opening and across a concave inner surface of the core; and securing the lining material at a peripheral edge of the core.

10. The method of claim 9 in which the central portion of the lining material is removed by cutting.

11. The method of claim 9 in which the lining material is secured to the core adjacent the central opening by stitching.

12. A method of using a hang-type earmuff, the earmuff having a truncated conical unitary seamless core of flexible plastic, the method comprising:

uniformly flexing a unitary seamless conical core throughout said core and inverting said unitary seamless conical core so that a concave inner surface is convex, a convex outer surface is concave and a cover on the convex outer surface of the core is loose, hanging the earmuff in its inverted condition on the wearer's ear; and reinverting the conical core.

13. A method of attaching a cover of sheet material to a hang-type earmuff, the earmuff having a truncated conical unitary seamless core of flexible plastic and a liner of sheet material on a concave inner surface of the core the method including:

placing the core and liner on a substantially conical fixture;

mating the core and liner with a sheet of cover material; and securing the cover material to the lining material outside a periphery of the core.

14. The attaching method of claim 13 including the step of trimming the lining and cover materials after they are secured.

15. The attaching method of claim 14 including the step of binding the edges of the lining and cover materials.

16. The attaching method of claim 13 in which the cover and lining materials are secured by sewing.

17. The attaching method of claim 15 in which the edges of the lining and cover materials are bound by stitching.

18. The attaching method of claim 13 including:

draping the sheet of cover material over the fixture;

placing the core and liner, with the core inverted and the liner outside, over the fixture and sheet of cover material, the fixture and cover material extending through the central opening of the core; and securing the cover material to the lining material outside the periphery of the core.

19. The attaching method of claim 18 in which the cover material is stitched to the lining material.

20. The attaching method of claim 13 including:

placing the core and liner over the fixture with the liner inside;

draping a sheet of cover material over the core and fixture; and sonic welding the cover material to the liner material outside the periphery of said core.

21. The attaching method of claim 20 including the step of trimming both the liner and cover materials concurrently with sonic welding of the materials.

22. The attaching method of claim 13 in which the cover material has a design and in which the cover material is secured in position with respect to the fixture to establish the position of the design with respect to the core.

23. The attaching method of claim 22 in which the fixture has a pin extending therefrom and the cover material is positioned by impaling it on the pin.

24. An earmuff comprising:

a seamless, unitary core formed of flexible plastic defining a central opening therein, the core having a truncated, conical shape;

a cover material secured to one surface of the plastic material thereby covering the central opening of the core; and a liner secured to the opposed side of the plastic material having a central opening in substantial alignment with the central opening of the core.

* * * * *